United States Patent [19]

Heckendorn

[11] 4,444,183

[45] Apr. 24, 1984

[54] HOOD

[76] Inventor: David E. Heckendorn, 4719 Third St., Bacliff, Tex. 77518

[21] Appl. No.: 327,418

[22] Filed: Dec. 4, 1981

[51] Int. Cl.³ .......................................... A61M 16/02
[52] U.S. Cl. .......................... 128/205.26; 128/204.18
[58] Field of Search .................... 128/204.18, 201.22, 128/205.26, 205.25, 200.24

[56] References Cited

U.S. PATENT DOCUMENTS

| D. 243,364 | 2/1977 | Miller | 128/205.26 |
| 2,418,473 | 4/1947 | Lambertsen et al. | 128/205.26 |
| 3,000,379 | 1/1960 | Viers | 128/205.26 |
| 3,799,163 | 3/1974 | Heath | 128/205.26 |
| 4,181,129 | 1/1980 | Cameto et al. | 128/205.26 |

FOREIGN PATENT DOCUMENTS 571307  1/1958  Italy .............................. 128/205.26

Primary Examiner—Henry J. Recla
Assistant Examiner—Kavin M. Reichle
Attorney, Agent, or Firm—Robert W. B. Dickerson

[57] ABSTRACT

A compartment, adapted to receive the head of a patient therein, which includes means for receiving a supply of oxygen or similar gas therein, the geometry being such that a continuous supply of such gas is provided adjacent the patient's face.

1 Claim, 2 Drawing Figures

HOOD

BACKGROUND OF THE INVENTION

Tents, inhalers, hoods, or the like, have long been used to provide a regulated atmosphere, commonly oxygen, to patients who have respiratory difficulty. Examples of the prior art found as a result of a search previously performed include devices shown in U.S. Pat. Nos. 2,600,501; 3,552,391; 3,000,379, 3,799,163; 2,389,293; 3,786,809; 4,181,129; and 2,508,050. It is essential that a supply of such regulated atmosphere be continuously provided in the area of the patients' face, i.e., nose and mouth. The mere inhalation of ambient atmosphere may not only be ineffective but may be dangerous. This invention has as its prime purpose such continuous provision to a patient, primarily to infant patients.

SUMMARY OF THE INVENTION

An open bottom polyhedron includes gas entry means at one end, and a cutout portion at the other end, to permit placing the device over a patient's neck or torso. Oftentimes such gas would be pure oxygen, however medication or other gases may be selectively provided. Gas entering through said entry is so deflected as to form a continuous reservoir at or adjacent said other end, such deflection being caused by the geometry of the device.

DESCRIPTION OF THE PREFERRED EMBODIMENT

Figure 1:
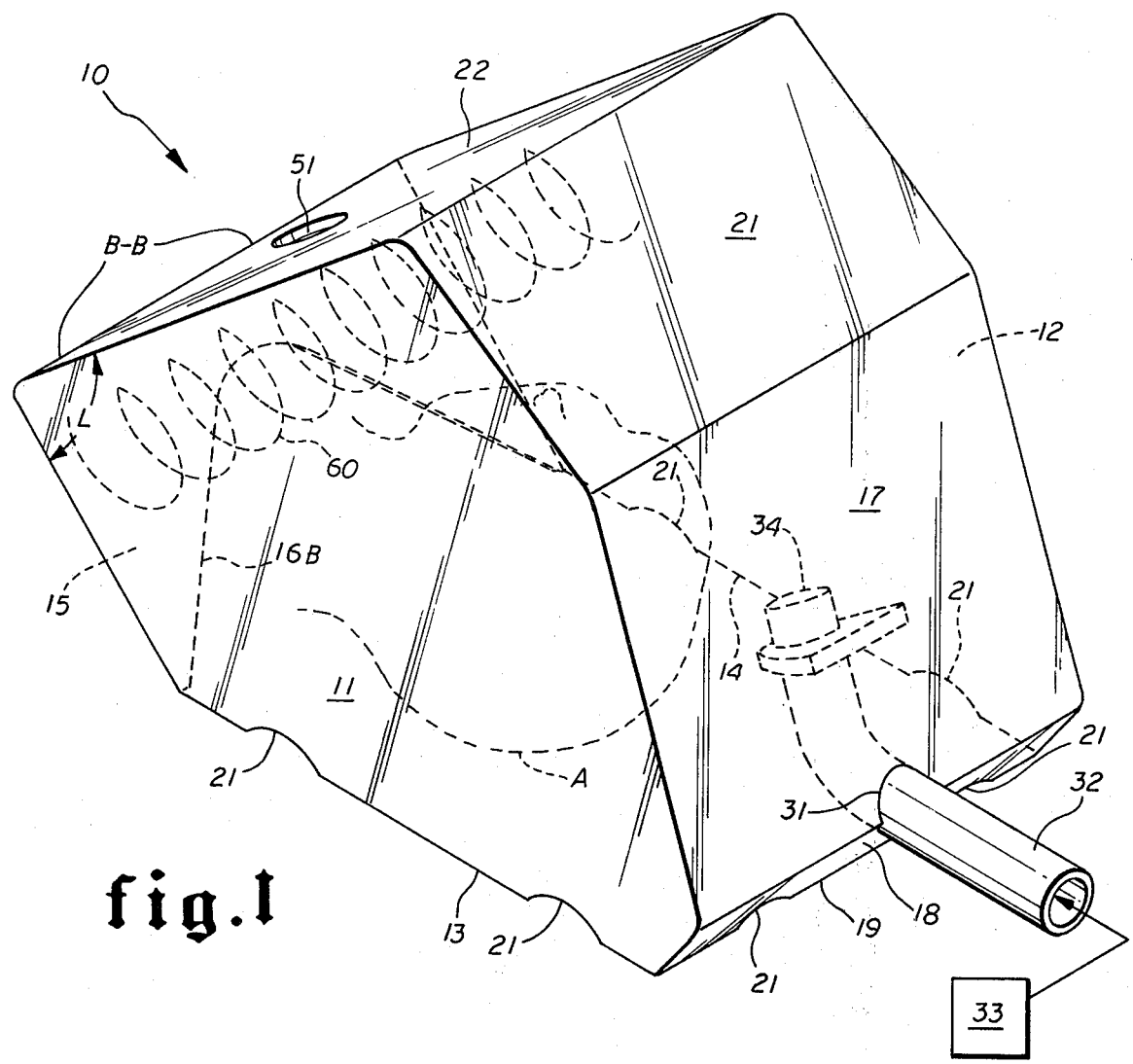
FIG. 1 is a perspective of the hood positioned over a patient's head.

Looking first at FIG. 1, the hood 10 would preferably be fabricated of a clear plastic material, and includes vertical sides 11 and 12, each of which have lower edges, 13, 14. One end of the hood is formed by wall 15, which wall includes V-shaped cut-out 16B so as to permit placing the hood over the neck or torso of a patient, with the patient's head "A", positioned therewithin. The other end of the hood 10 is formed by intersecting planar members 17, 18, the latter member having a lower edge 19. All of lower edges 13, 14 and 19, include semicircular passageways 21 therethrough, to accomodate monitors, I-V lines and the like. The bottom of the hood is obviously open, to allow it to be placed over a patient. The top of the hood is formed by intersecting planar members 21, 22. Note that the intersection B-B between front wall 15 and top portion 22 forms a curved intersection. Also note that the angle "L" between said walls 15, 22 approaches 90 degrees.

Gas inlet 31 is provided at or near the intersection of end wall positions 17, 18, to accomodate flexible gas conduit 32. One end of said conduit would be communicatingly connected with a source of gas 33, while the other end would form a spout 34, upwardly curved, so as to direct such gas against planar surface 21. An exhaust aperture 51 is provided upper wall portion 22.

Figure 2:
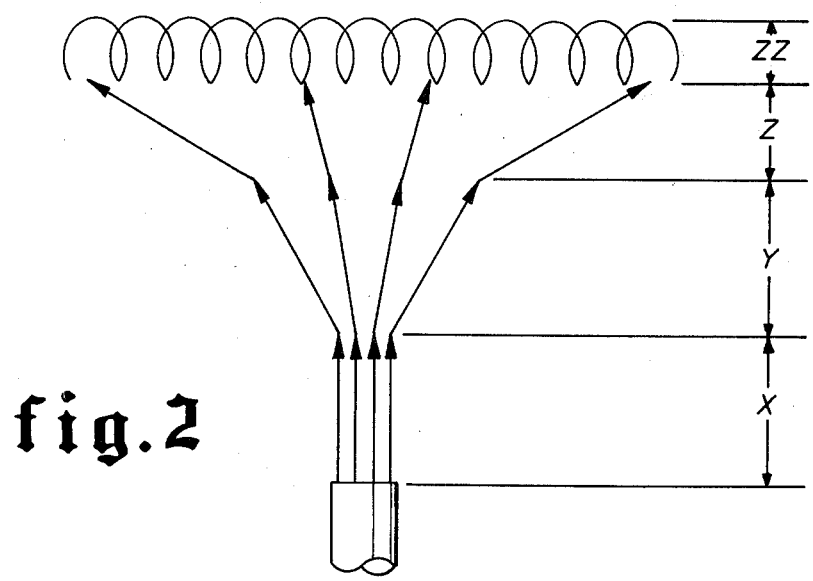
FIG. 2 is a diagramatic illustration of paths followed by the gas.

The ultimate destination of the incoming gas, is a reservoir or cylinder of gas, identified by the numeral 60, and depicted as a spiral extending the width of the device, and approximately between the curved intersection B-B, and the patient's face. The approximate path believed to be followed by the gas is illustrated by the arrows of FIG. 2. Incoming gas would pass through conduit 32, to exit upwardly through spout 34, where it would angularly strike upper wall portion 21, and be deflected thereby. The course of the gas within device 10, between spout 34 and wall portion 21 is illustrated by portion "X". On striking wall portion 21, the gas would be angularly diverted and spread, this portion of its movement being illustrated by chart Section "Y". Subsequently, the gas would strike the underside of upper wall section 22 and further spread. Such movement is illustrated by chart section "Z". Thus far, the gas has tended to strike the wall sections at acute angles, and follow a path somewhat tangential to the walls' under surfaces. Thereafter the gas, which by now would extend substantially the width of the hood, would encounter front wall 15, including the curved intersection B-B. Walls 22, 15 are near normal to each other. The reservoir or cylinder of gas 60 which is operatively formed, is believed to be caused by a combination of (1) the turbulence resulting from the gas striking wall 15 which is nearly perpendicular to its path, and (2) the curved intersection of walls 15 and 22 i.e., from the hood's geometry. In any case, the location of such reservoir provides a steady supply for the patient at the location where it is needed. Excess regulated gas and ambient air may exhaust through port 51.

Although only a single embodiment has been described, it should be obvious that numerous modifications would be possible by one skilled in the art without departing from the spirit of the invention, the scope of which is limited only by the following claims.

I claim:

1. A hood comprising:
    a compartment open at the bottom thereof, said compartment including;
        a front planar wall having a portion thereof adapted to be placed over a patient, a rear planar wall means comprising at least one planar surface, said rear planar wall means having means for receiving gas inlet means therethrough, means for causing gas entering said receiving means to form a continuous reservoir of gas adjacent said front planar wall, said reservoir forming means including a pair of connecting upper wall planar portions, one of which upper wall planar portions is linked to said front planar wall and the other of which is linked to said one rear planar surface, said upper wall planar portions forming an obtuse angle therebetween, said other upper wall planar portion and said one rear planar surface forming an obtuse angle therebetween, and said one upper wall planar portion and said front planar wall having a curved juncture and being approximately perpendicular to each other, and
    gas inlet means positionable within said gas inlet receiving means, said gas inlet means being so positionable as to direct gas at an acute angle relative to said other upper wall planar portion, said pair of upper wall planar portions being so angularly related that gas from said gas inlet means striking said other upper wall planar portion at an acute angle will thereafter strike said one upper wall planar portion at an acute angle, and said one upper wall planar portion and said front planar wall are so angularly related that said gas from said gas inlet means striking said one upper wall planar portion will thereafter strike said front wall in an approximately perpendicular manner.

* * * * *